US011040110B2

(12) United States Patent
Song et al.

(10) Patent No.: US 11,040,110 B2
(45) Date of Patent: *Jun. 22, 2021

(54) POLYPEPTIDE COMPLEX COMPRISING NON-PEPTIDYL POLYMER HAVING THREE FUNCTIONAL ENDS

(71) Applicant: HANMI SCIENCE CO., LTD., Hwaseong-si (KR)

(72) Inventors: Dae Hae Song, Seoul (KR); Jae Hee Shin, Suwon-si (KR); Mi Ji Lee, Incheon (KR); Sung Hee Hong, Suwon-si (KR); Se Chang Kwon, Seoul (KR); Gwan Sun Lee, Seoul (KR)

(73) Assignee: HANMI SCIENCE CO., LTD., Hwaseong-si (KR)

( * ) Notice: Subject to any disclaimer, the term of this patent is extended or adjusted under 35 U.S.C. 154(b) by 49 days.

This patent is subject to a terminal disclaimer.

(21) Appl. No.: 16/057,454

(22) Filed: Aug. 7, 2018

(65) Prior Publication Data

US 2018/0360983 A1 Dec. 20, 2018

Related U.S. Application Data

(60) Continuation of application No. 14/873,321, filed on Oct. 2, 2015, now Pat. No. 10,071,171, which is a division of application No. 13/055,406, filed as application No. PCT/KR2009/004114 on Jul. 23, 2009, now Pat. No. 9,636,420.

(30) Foreign Application Priority Data

Jul. 23, 2008 (KR) ........................ 10-2008-0071766

(51) Int. Cl.
| | | |
|---|---|---|
| *A61K 47/68* | (2017.01) | |
| *A61K 47/60* | (2017.01) | |
| *C07K 19/00* | (2006.01) | |
| *A61P 43/00* | (2006.01) | |
| *A61P 31/00* | (2006.01) | |
| *A61P 5/00* | (2006.01) | |
| *A61P 5/50* | (2006.01) | |
| *C07K 14/59* | (2006.01) | |

(52) U.S. Cl.
CPC .......... *A61K 47/6803* (2017.08); *A61K 47/60* (2017.08); *A61K 47/6811* (2017.08); *A61K 47/6889* (2017.08); *C07K 14/59* (2013.01); *C07K 19/00* (2013.01); *C07K 2319/31* (2013.01)

(58) Field of Classification Search
CPC ............ A61K 47/6803; A61K 47/6889; A61K 47/60; A61K 47/6811; C07K 14/59; C07K 19/00; A61P 5/50; A61P 5/00; A61P 43/00; A61P 31/00
See application file for complete search history.

(56) References Cited

U.S. PATENT DOCUMENTS

| | | | |
|---|---|---|---|
| 6,660,843 B1 | 12/2003 | Feige et al. | |
| 6,756,480 B2 | 6/2004 | Kostenuik et al. | |
| 6,989,147 B2 | 1/2006 | Fisher et al. | |
| 8,106,154 B2 | 1/2012 | Holmes et al. | |
| 9,636,420 B2 * | 5/2017 | Song .................. | A61K 47/6811 |
| 10,071,171 B2 * | 9/2018 | Song .................. | A61K 47/6889 |
| 2003/0211078 A1 * | 11/2003 | Heavner .............. | C07K 14/505 |
| | | | 424/85.1 |
| 2004/0023848 A1 | 2/2004 | Boehm | |
| 2006/0275254 A1 | 12/2006 | Kim et al. | |
| 2007/0041967 A1 | 2/2007 | Jung et al. | |

FOREIGN PATENT DOCUMENTS

| | | |
|---|---|---|
| AR | 065639 A1 | 6/2009 |
| AU | 2009274738 B2 | 1/2010 |
| CN | 1723219 A | 1/2006 |
| JP | 2007-531513 A | 11/2007 |
| JP | 2007-536211 A | 12/2007 |
| JP | 2007-537992 A | 12/2007 |
| WO | 93/02105 A1 | 2/1993 |
| WO | 94/11399 A1 | 5/1994 |
| WO | 2004/054615 A1 | 7/2004 |
| WO | 2005047337 A1 | 5/2005 |

(Continued)

OTHER PUBLICATIONS

Rudikoff et al., PNAS 79: 1979-1983 (Year: 1982).*
Gennaro et al in Remington's Pharmaceutical Sciences, eighteenth edition, pp. 1300-1329 (Year: 1990).*
Ahrends, "Identifying an Interaction Site Between MutH and the C-terminal Domain of MutL by Crosslinking Affinity Purification, Chemical Coding and Mass Spectrometry," Nucleic Acids Research, 2006, vol. 34, No. 10, pp. 3169-3180.
Chinese Patent Office, Chinese Office Action issued in corresponding CN Application No. 200980127997.4, dated Nov. 12, 2012.
Dinesen et al., "Targeting Nanomedicines in the Treatment of Crohn's Disease: Focus on Certolizumab Pegol (CDP870)," International Journal of Nanomedicine, 2007, pp. 39-47.
European Patent Office, Supplementary European Search Report issued in corresponding EP Application No. 09 80 0577.0, dated Dec. 22, 2011.

(Continued)

*Primary Examiner* — Phuong Huynh
(74) *Attorney, Agent, or Firm* — Sughrue Mion, PLLC

(57) ABSTRACT

Disclosed is a protein complex, comprising a physiologically active polypeptide, a dimeric protein and a non-peptidyl polymer having three functional ends (3-arm), with the linkage of both the physiologically active polypeptide and the dimeric protein to the 3-arm non-peptidyl polymer via respective covalent bonds. The protein complex guarantees the long acting activity and biostability of a physiologically active polypeptide. Having the ability to maintain the bioactivity of physiologically active polypeptides or peptides highly and to significantly improve the serum half life of the polypeptides or peptides, the protein complex can be applied to the development of sustained release formulations of various physiologically active polypeptide drugs. Also, it utilizes raw materials including the physiologically (Continued)

active polypeptides without significant loss, thereby increasing the production yield. Further, it can be easily purified.

26 Claims, 3 Drawing Sheets

(56) References Cited

FOREIGN PATENT DOCUMENTS

| WO | 2006/116156 | A2 | 11/2006 |
|---|---|---|---|
| WO | 2007/062177 | A2 | 5/2007 |
| WO | 2008/034124 | A2 | 3/2008 |
| WO | 2008/082274 | A1 | 7/2008 |

OTHER PUBLICATIONS

Intellectual Property Office of the Philippines, Communication dated Aug. 6, 2014, issued in corresponding Philippine application No. 1/2011/500075.

Japanese Patent Office, Japanese Office Action issued in corresponding JP Application No. 2011-519993, dated Feb. 12, 2013.
Patent Cooperation Treaty, International Search Report issued in corresponding International Application No. PCT/KR2009/004114, dated Mar. 9, 2010.
Studdert et al., "Insights into the Organization and Dynamics of Bacterial Chemoreceptor Clusters Through in vivo Corsslinking Studies," PNAS, 2005, vol. 102, No. 43, pp. 15623-15628.
Ton et al., "Phase I Evaluation of CDP791, a PEGylated Di-Fab' Conjugate that Binds Endothelial Growth Factor Receptor 2," Clin Cancer Res, 2007, vol. 13, No. 23, pp. 7113-7118.
Roberts et al, Advanced Drug Delivery Reviews 54: 459-476, 2002.
Argentina Patent Office: Argentina Office Action issued in corresponding AR Application No. P090102798, dated Jun. 30, 2016.
Skolnick et al., Trends in Biotechnology, vol. 18, pp. 34-39, 2000.
Burgess et al., Journal of Cell Biology, vol. 111, pp. 2129-2138, 1990.
Lazar et al., Molecular and Cellular Biology, vol. 8, pp. 1247-1252, 1988.

\* cited by examiner

[Figure 1]
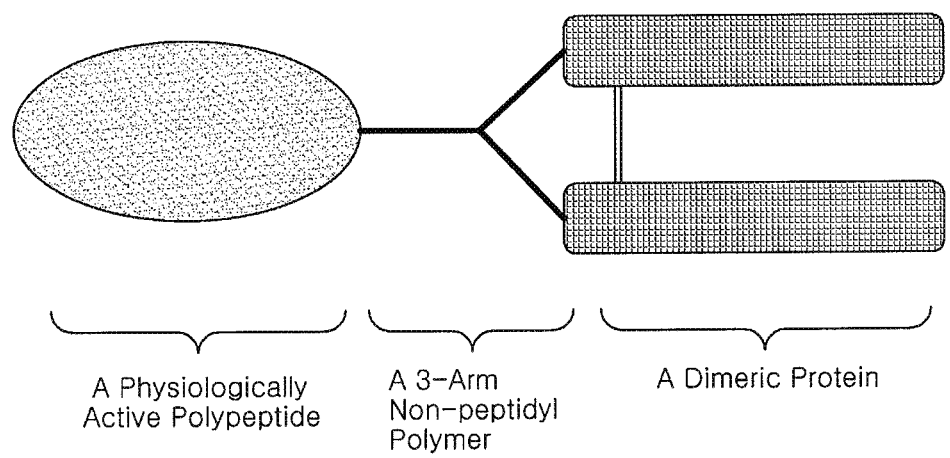
A Physiologically Active Polypeptide | A 3-Arm Non-peptidyl Polymer | A Dimeric Protein

[Figure 2]
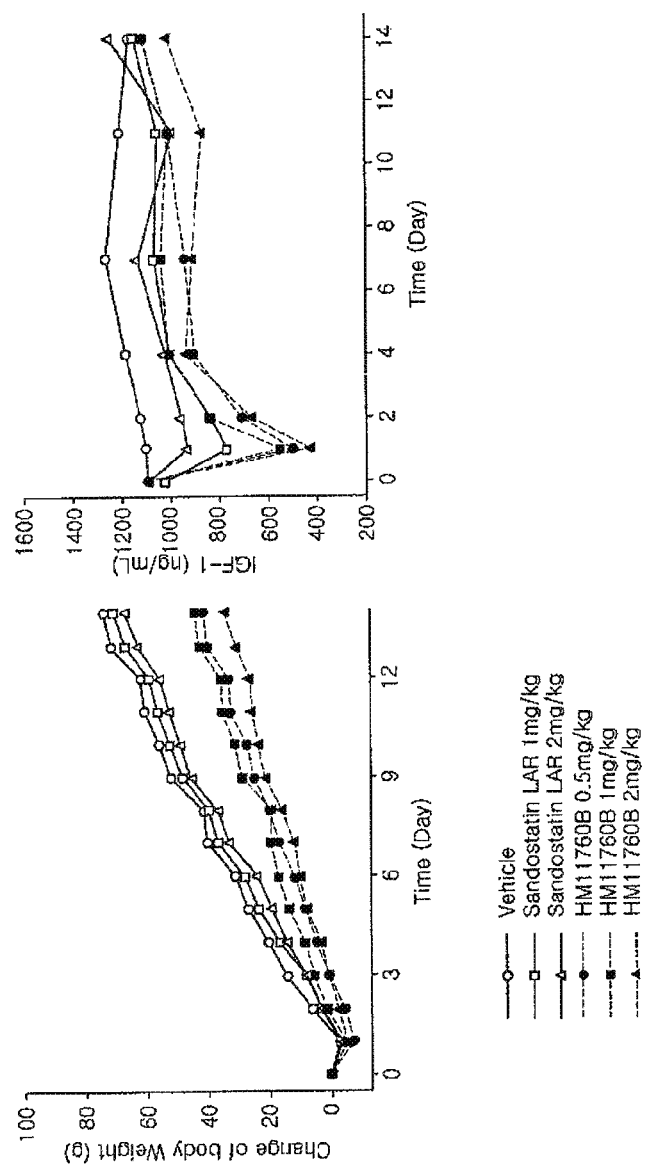

[Figure 3]
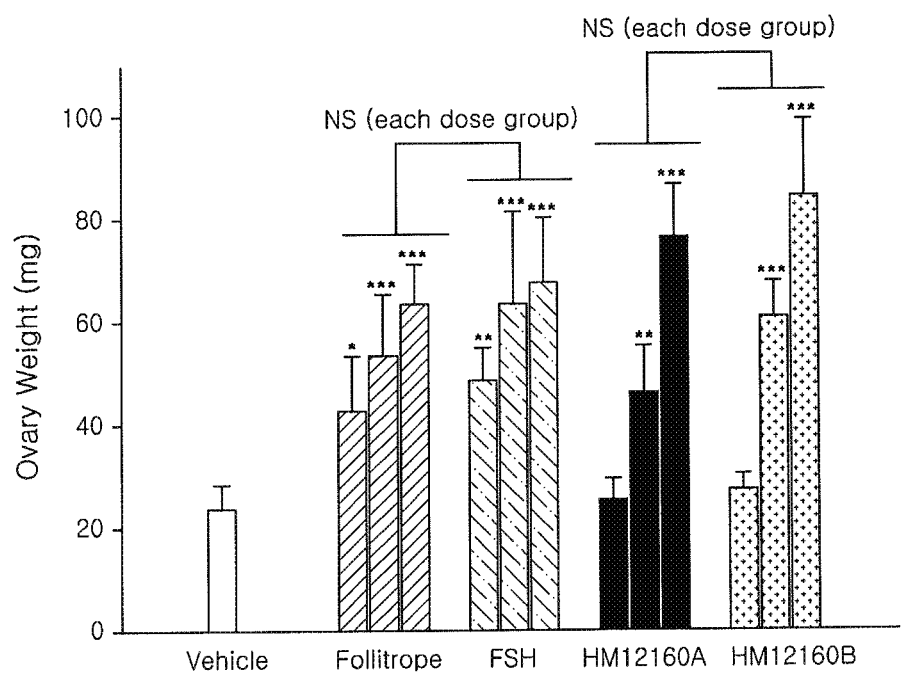

POLYPEPTIDE COMPLEX COMPRISING NON-PEPTIDYL POLYMER HAVING THREE FUNCTIONAL ENDS

CROSS REFERENCE TO RELATED APPLICATIONS

The present application is a continuation of U.S. application Ser. No. 14/873,321 filed Oct. 2, 2015, now U.S. Pat. No. 10,071,171, issued Sep. 11, 2018, which is a divisional of U.S. application Ser. No. 13/055,406 filed Apr. 14, 2011, now U.S. Pat. No. 9,636,420, issued May 2, 2017, which is a National Stage of International Application No. PCT/KR2009/004114, filed on Jul. 23, 2009, which claims the benefit of priority from Korean Patent Application No. KR 10-2008-0071766, filed on Jul. 23, 2008, the contents of which are herein incorporated by reference in their entirety.

TECHNICAL FIELD

The present invention relates to a protein complex which allows the long acting activity of a physiologically active polypeptide with a dimeric protein. More particularly, the present invention relates to a protein complex in which a physiologically active polypeptide and a dimeric protein are linked to a non-peptidyl polymer having three functional ends (3-arm) via respective covalent bond, and a method for preparing the same.

BACKGROUND ART

Due to low stability, polypeptides are generally apt to denature and be degraded by proteinases and lose their activity. On the other hand, peptides are relatively small in size so that they are readily excreted through the kidney.

In order to maintain desired blood level concentrations and titers thereof, thus, protein medicines comprising polypeptides or peptides as active ingredients need to be frequently administered. However, because protein medicines are, for the most part, in a form suitable for injections, the maintenance of physiologically active polypeptides or peptides at appropriate blood levels requires frequent injections, causing significant pain to the patient. In order to overcome these problems, attempts have been made to provide maximum medicinal effects by increasing the stability of protein medicines in the blood and by maintaining blood medicine levels high for a long period of time. These long-lasting protein medicine agents are required not only to increase the stability of the protein medicines and maintain sufficient titers of the medicines themselves, but also to not cause immune responses in the patients.

Conventionally, highly soluble polymers such as polyethyleneglycol (PEG) are chemically grafted onto the surface of proteins with the aim of stabilizing the proteins, preventing the contact of proteinases with the proteins, and suppressing the renal loss of small-size peptides. Grafted to specific or a variety of different sites on proteins, PEG is useful for the stabilization and hydrolysis prevention of proteins without creating noteworthy side effects. In addition, grafted PEG increases the molecular weight of the proteins, thereby restraining renal loss of the proteins and maintaining the physiological activity of the proteins.

For example, WO 2006/076471 describes the use of B-type natriuretic peptide (BNP) in the treatment of congestive heart failure. BNP binds to natriuretic peptide receptor A (NPR-A) to trigger the synthesis of cGMP, thereby reducing arterial blood pressures. When PEGylated, BNP is described as elongating the physiological activity thereof for a long period of time. U.S. Pat. No. 6,924,264 also discloses an increase in the active period of exendin-4 by grafting PEG onto a lysine residue.

In order to increase the physiological activity thereof, a medicinal polypeptide is linked to both of the terminals of PEG to form a bis-conjugate (U.S. Pat. No. 5,738,846). On the other hand, two different medicinal proteins are linked to respective terminals of PEG to form a protein complex which have two different physiological activities (WO 92/16221). However, no significance was found in these protein drugs in terms of activity maintenance.

Also, it was reported that a fusion protein in which G-CSF and human albumin were linked to one PEG increased in stability (Kinstler et al., Pharmaceutical Research 12(12): 1883-1888, 1995). However, the modified drug with a G-CSF-PEG-albumin structure was found to increase in residence time by only about four times, compared to natural drugs alone, and to be only slightly increased in serum half life. Thus, the modified drug is not practically applied as a lasting agent.

When coupled with PEG, peptides become so stable as to extend the persistence thereof in vivo. However, when given high molecular weights, PEG makes the titer of the physiological active peptide significantly low and decreases in reactivity with peptides, resulting in a low yield.

An alternative for increasing the stability of physiologically active proteins in vivo takes recourse to gene recombination. A gene coding for a protein highly stable in the blood is linked to a gene coding for a physiologically active protein of interest, followed by transformation into animal cells which are then cultured to produce a fusion protein.

For example, a fusion protein in which albumin or a fragment thereof, known to be the most effective in stabilizing proteins thus far, is fused to a physiological active protein of interest has been reported (WO 93/15199 and 93/15200, EP Publication No. 413,622). Also, a fusion protein of interferon alpha and albumin, produced from yeast by Human Genome Sciences (trade name: Albuferon™) increased its serum half-life from 5 hrs to 93 hrs, but suffers from the critical disadvantage of being decreased in bioactivity to less than 5% of that of naive interferon (Osborn et al., J. Phar. Exp. Ther. 303(2): 540-548, 2002).

As for peptides, their modifications are mentioned in WO 02/46227 which discloses that GLP-1, exendin-4 and analogs thereof are fused to human serum albumin or immunoglobulin fragments (Fc) using genetic recombination techniques and in U.S. Pat. No. 6,756,480 which discloses fusion proteins of parathyroid hormone (PTH) or analogs thereof and immunoglobulin fragments (Fc). These approaches can overcome low pegylation yield and non-specificity, but are disadvantageous in that serum half life is not significantly increased and in some cases, low titers result. Various peptide linkers are used to maximally increase serum half life, but show the high possibility of causing immune responses. When given, a peptide having a disulfide bond, such as BNP, is highly likely to induce misfolding and thus is difficult to apply.

Other various fusion proteins are also known to be prepared by linking the Fc domain of immunoglobulin to interferon (Korean Patent Publication No. 2003-9464), interleukin-4 receptor, interleukin-7 receptor or erythropoietin receptor (Korean Patent No. 249572) through genetic recombination. PCT Patent Publication No. WO 01/03737 discloses a fusion protein in which a cytokine or a growth factor is linked through an oligopeptide linker to an Fc fragment of immunoglobulin. U.S. Pat. No. 5,116,964 describes LHR (lymphocyte cell surface glycoprotein) or CD4 protein which is fused to the amino or carboxy end of an immunoglobulin Fc domain using a genetic recombination technique. Also, U.S. Pat. No. 5,349,053 discloses a fusion protein in which IL-2 is linked to an immunoglobulin Fc domain. Many other Fc fusion proteins constructed using genetic recombination techniques are disclosed, examples of which include a fusion protein of an immunoglobulin Fc domain with interferon-beta or a derivative thereof (PCT Patent Publication No. WO 00/23472), an immunoglobulin Fc domain with an IL-5 receptor (U.S. Pat. No. 5,712,121), an immunoglobulin G4 Fc domain with interferon alpha (U.S. Pat. No. 5,723,125) and an immunoglobulin G2 Fc domain with a CD4 protein (U.S. Pat. No. 6,451,313). On the other hand, U.S. Pat. No. 5,605,690 teaches the use of a modified immunoglobulin Fc domain in the production of fusion proteins. For example, immunoglobulin Fc with amino acid residues modified particularly to complement binding sites or receptor binding sites is used to produce a TNFR-IgG1 Fc fusion protein using a genetic recombination method. Other fusion proteins of the modified immunoglobulin Fc domain which are produced using gene recombination techniques are disclosed in U.S. Pat. Nos. 6,277,375, 6,410,008 and 6,444,792.

Immunoglobulins function as antibodies, showing antibody-dependent cell cytotoxicity (ADCC) or complement-dependent cytotoxicity (CDC) and the sugar chains present in the immunoglobulin Fc domain are reported to play an important role in ADCC and CDC (Burton D., Molec. Immun. 22, 161-206, 1985). Immunoglobulins themselves, when free of sugar chains, are known to be similar in serum half life to the immunoglobulins having sugar chains, but to have a 10- to 1000-fold decrease in complement binding force and receptor binding force (Waldmann H., Eur. J. Immunol. 23, 403-411, 1993; Morrison S., J. Immunol. 143, 2595-2601, 1989).

U.S. Pat. No. 6,660,843 discloses the fusion of an Fc domain with a peptide of interest through a linker and the production of the fusion protein in *E. coli* using a gene recombination technique. For use in preparing complexes, a linker allows the selection of the conjugation sites between two proteins of interest and the orientations thereof, and enables the production of complexes in the form of homogenous or heterogenous monomers, dimers or multimers. In addition, when using this method, the complexes can be produced at a lower cost than when using mammal cells. In addition, the complexes may be produced in sugar chain-free forms. Because of the concomitant production of both the protein of interest and the immunoglobulin Fc domain in *E. coli*, however, this method is difficult to apply to a target protein when the native form of the target protein has a sugar chain. Taking advantage of inclusion bodies, this method is highly apt to induce misfolding. In the Fc fusion proteins produced using the genetic recombination techniques, fusion is possible only at specific sites, that is, an amino or carboxy terminus of the immunoglobulin Fc domain. The Fc fusion proteins are expressed only in homogenous dimeric forms, but not in monomeric forms. Further, fusion is possible only between glycosylated proteins or between aglycosylated proteins, but impossible between glycosylated proteins and aglycosylated proteins. If present, an amino acid sequence newly formed as a result of the fusion may induce an immune response. Moreover, the linker may be sensitive to enzymatic degradation.

In the development of fusion proteins using immunoglobulin Fc domains, nowhere has an attempt been made to give complexes of target proteins with human native Fc through a crosslinker in previous reports. Immunoglobulin Fc domains can be produced in mammal cells or *E. coli* using genetic recombination techniques, but nowhere has an attempt been made to produce only native immunoglobulin Fc domains free of target proteins at high yield and to apply them to lasting forms in previous reports. In addition, no attempts have been made to produce complexes of the recombinant immunoglobulin Fc with target proteins through crosslinkers.

As such, a variety of different methods have been performed in order to conjugate physiologically active polypeptides with polymers. In conventional methods, polypeptides can be improved in stability, but with significant reduction in activity, or can be improved in activity irrespective of stability. Therefore, there is still a need for a method that can increase the stability of protein medicines with a minimum reduction in modification-induced activity.

In this context, the present inventors developed a protein complex which is improved in serum half life with high activity by linking an immunoglobulin and a physiologically active polypeptide respectively to opposite termini of a non-peptidyl linker as disclosed in Korean Patent Nos. 10-0725315 and 10-0775343, which are incorporated by reference in their entirety.

A protein complex in which an immunoglobulin and a physiologically active polypeptide are respectively linked to opposite termini of a non-peptidyl polymer is conventionally prepared by linking a non-peptidyl polymer preferentially with a physiologically active polypeptide and then with an immunoglobulin Fc domain. However, this conventional preparation method produces lots of undesirable impurities, as well, resulting in losing a large quantity of the physiologically active polypeptide. That is, the conventional method is economically unfavorable upon the industrial application thereof and the resulting complex must be purified in a somewhat complicated manner. In the case where the physiologically active polypeptide is in the form of a dimer, it produces a bridge form with a non-peptidyl polymer at both termini so that it cannot complex with an immunoglobulin Fc or can complex but at very low yield. On the other hand, when an immunoglobulin Fc domain is first linked to a non-peptidyl polymer, similar problems occur as well. Because an immunoglobulin Fc is a homodimer with two N-termini in close vicinity to each other, respective links are formed between the two N-termini of the immunoglobulin Fc and the opposite termini of the non-peptidyl polymer to produce a bridge form, so that no functional ends remain to be reacted with the physiologically active polypeptide. Accordingly, the production yield significantly decreases.

DISCLOSURE

Technical Problem

Leading to the present invention, intensive and thorough research into protein complexes, conducted by the present inventors, aiming to overcome the problems encountered in the prior art, resulted in the finding that the use of 3-arm non-peptidyl polymer as a linker in preparing a protein complex composed of a dimeric protein and a physiologically active polypeptide prevents the loss of the physiologically active polypeptide to significantly increase the production yield, allows the complex to be purified with a simple method, and gives structural stability to the protein complex to extend the serum half life while at the same time maintaining the biological activity thereof.

Technical Solution

It is therefore an object of the present invention to provide a protein complex in which a physiologically active polypeptide, a 3-arm non-peptidyl polymer, and a dimeric protein are linked via covalent bonds, and a method for preparing the same.

It is another object of the present invention to provide a sustained protein drug agent comprising a protein complex which extends the serum half life of a physiologically active polypeptide while maintaining the biological activity thereof.

Advantageous Effects

Having a structure in which a physiologically active polypeptide and a dimeric protein are linked to a 3-arm non-peptidyl polymer via covalent bonds, the protein complex of the present invention can maintain a high blood concentration of the active polypeptide over a long period of time producing stable medicinal effects.

In addition, the method for preparing the protein complex in accordance with the present invention can greatly reduce the amount of physiologically active polypeptide required by the conventional method using a 2-arm non-peptidyl polymer and enjoys, over the conventional method, the advantage of introducing more simple purification methods and significantly increasing the production yield. Especially, persistent protein complexes with dimeric, physiologically active polypeptides were preferably prepared using the method of present invention.

DESCRIPTION OF DRAWINGS

FIG. 1 shows representative figure of a protein complex using a non-peptidyl polymer having three functional ends (3-arm).

FIG. 2 shows in vivo efficacies of the immunoglobulin Fc-3 arm PEG-Octreotide(N) complex in plots (HM11760B: immunoglobulin Fc-3 arm PEG-Octreotide(N) complex, Sandostatin-LAR: a sustained release formulation of octreotide).

FIG. 3 shows in vivo efficacy of the immunoglobulin Fc-3 arm PEG-FSH(N) complex (HM12160A: immunoglobulin Fc-2 arm PEG-FSH(N) complex, HM12160B: immunoglobulin Fc-3 arm PEG-FSH(N) complex).

BEST MODE

In accordance with an aspect thereof, the present invention is directed to a protein complex in which a physiologically active polypeptide and a dimeric protein are covalently linked to a 3-arm non-peptidyl polymer.

As used herein, the term "protein complex" or "complex" is intended to refer to a structure composed of at least one physiologically active polypeptide, at least one 3-arm non-peptidyl polymer and at least one dimeric protein, with interconnection via covalent bonds among them. In order to differentiate itself from a "complex", the term "conjugate" is used herein to refer to a structure in which only pairs of the physiologically active polypeptide, the non-peptidyl polymer and the dimeric protein are interconnected via a covalent bond.

The protein complex of the present invention is a protein drug which is modified to increase the persistence thereof in vivo and minimally reduce the biological activity thereof. The present invention features the use of a 3-arm non-peptidyl polymer to connect a physiologically active polypeptide and a dimeric protein therethrough to form a protein complex, thereby allowing the application of a preparing method by which the loss of the physiologically active polypeptide can be prevented and the protein complex can be so structurally stable as to be purified simply.

As used herein, the term "dimeric protein" means a protein with two N-termini. Preferred is an immunoglobulin Fc domain which can be used as a carrier. Physiologically active homodimers or heterodimers are also included within the scope of the dimeric protein.

An immunoglobulin Fc domain is stable enough to be used as a carrier for a drug because it is a biodegradable polypeptide which is metabolized in vivo. In addition, thanks to relatively small molecular weights, the immunoglobulin Fc domain has advantages over total immunoglobulin molecules in terms of the preparation, purification and yield of the complex. Further, because it is free of Fab that is highly different in amino acid sequence from one antibody to another, Fc strongly promotes the homogeneity of the complex and is expected to reduce the induction of antigenicity.

The term "immunoglobulin Fc domain", as used herein, is intended to indicate heavy chain constant domain 2 ($C_H2$) and heavy chain constant domain 3 ($C_H3$) which is free of heavy and light chain variable domains, heavy chain constant domain 1 ($C_H1$) and light chain constant domain 1 ($C_L1$) and may comprise a hinge region. The immunoglobulin Fc domain of the present invention may be an extended Fc domain which further comprises a part or total heavy chain constant domain 1 ($C_H1$) and/or light chain constant domain 1 ($C_L1$) and is free of the heavy and light chain variable domains if it guarantees an effect substantially the same as or higher than that of the native form. Alternatively, the Fc domain may be a truncated form of $C_H2$ and/or $C_H3$ which lacks a significant part of the corresponding amino acid sequence. To sum up, the immunoglobulin Fc domain of the present invention may be 1) $C_H1$ domain, $C_H2$ domain, $C_H3$ domain and $C_H4$ domain, 2) $C_H1$ domain and $C_H2$ domain, 3) $C_H1$ domain and $C_H3$ domain, 4) $C_H2$ domain and $C_H3$ domain, 5) a combination of one or more domains and an immunoglobulin hinge region (or a part of hinge) or 6) a dimer composed of each light chain constant domain and a light chain constant domain.

In addition, the term "immunoglobulin Fc domain", as used herein, is intended to cover not only native amino acid sequences but also mutants thereof. The amino acid sequence mutant means an amino acid sequence different from the native sequence by deletion, insertion, non-conservative or conservative substitution of one or more amino acid residues or combinations thereof. For example, the amino acid residues at positions 214 to 238, 297 to 299, 318 to 322, or 327 to 331 of IgG Fc, which are known to play an important role in antibody binding, may be modified so as to be used as suitable binding sites. In addition, possible are various mutants which, for example, lack a residue forming a disulfide bond or several N-terminal amino acids of the native Fc, or have an additional methionine residue at the N terminus of the native Fc. Further, effector functions may be eliminated by removing a complement binding motif, e.g., C1q binding motif, or an ADCC (antibody-dependent cell mediated cytotoxicity) motif. Reference may be made to WO 97/34631 and WO 96/32478 concerning the preparation of amino acid sequence mutants of immunoglobulin Fc domains.

Amino acid substitutions which do not alter the activity of native proteins or peptides as a whole are known in the art (H. Neurath, R. L. Hill, The Proteins, Academic Press, New York, 1979). Most typical substitutions occur between Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. If necessary, the amino acids may undergo a modification, such as phosphorylation, sulfation, acrylation, glycosylation, methylation, farnesylation, acetylation, amidation, etc.

The above-described Fc mutants are preferably functional equivalents to their natural forms, thus being similar in biological activity, with an improvement in structural stability against heat and pH.

The Fc domain may be a native form isolated from humans and other animals including cows, goats, pigs, mice, rabbits, hamsters, rats and guinea pigs, or may be a recombinant or a derivative thereof, obtained from transformed animal cells or microorganisms. In the former case, total immunoglobulin is isolated from humans or animals, followed by protease treatment. When treated with papain, the total immunoglobulin is divided into Fab and Fc. Pepsin cleaves total immunoglobulin into pF'c and F(ab)2. From these fragments, Fc or pF'c can be separated using size-exclusion chromatography. Preferred is a recombinant immunoglobulin Fc domain derived from the human Fc domain in microorganisms.

The immunoglobulin Fc domain useful in the present invention may have a sugar chain less than, equal to, or longer in length than the native Fc domain, or may not have sugar chains. The addition, reduction or removal of the immunoglobulin Fc sugar chain may be achieved using a typical technique, such as a chemical technique, an enzymatic technique or a genetic recombination technique using microorganism. A deglycosylated immunoglobulin Fc domain is significantly reduced in the binding force of the complement (C1q) and has little or no antibody-dependent cell-mediated cytotoxicity or complement-dependent cytotoxicity, and thus induces no unnecessary immune responses. In this context, deglycosylated or aglycosylated immunoglobulin Fc domains preferentially coincide with the intended function as drug carriers.

As used herein, the term "deglycosylation" refers to the enzymatic removal of a sugar chain from the native Fc. The term "aglycosylation" refers to the absence of sugar chains in the Fc domain because it is produced in eucaryotes and preferably in *E. coli*.

The immunoglobulin Fc domain may originate from animals including humans, cows, goats, pigs, mice, rabbits, hamsters, rats and guinea pigs with a preference for human origin. In addition, the immunoglobulin Fc domain useful in the present invention may be derived from among IgG, IgA, IgD, IgE, IgM and combinations thereof or hybrids thereof. Preferably, it is derived from IgG or IgM, which are more abundant than the other types of immunoglobulin, and most preferably from IgG which is known to extend the serum half life of ligand binding proteins.

Also, the immunoglobulin Fc domain may be in the form of dimers or multimers (combinations of immunoglobulin Fc), each comprising glycosylated immunoglobulins composed of domains of the same origin.

The term "combination", as used herein, means that polypeptides encoding single-chain immunoglobulin Fc fragments of the same origin are linked to a single-chain polypeptide of a different origin to form a dimer or multimer. That is, a dimer or a multimer may be prepared by combining two or more fragments selected from among the Fc fragments of IgG Fc, IgA Fc, IgM Fc, IgD Fc and IgE Fc.

The term "hybrid", as used herein, means that sequences encoding two or more immunoglobulin Fc fragments of different origins are present in a single-chain immunoglobulin Fc fragment. In the present invention, various hybrid forms are possible. For example, the Fc domain is composed of one to four different domains selected from $C_H1$, $C_H2$, $C_H3$ and $C_H4$ of IgG Fc, IgM Fc, IgA Fc, IgE Fc and IgD Fc and may comprise a hinge region.

IgG is also further divided into the subclasses of IgG1, IgG2, IgG3 and IgG4 and their combinations or hybrids are permitted in the present invention. Preferable is an Fc domain of IgG2 or IgG4, with the highest preference being given for an Fc domain of IgG4 free of effector functions such as complement-dependent cytotoxicity (CDC).

Accordingly, an aglycosylated Fc domain of human IgG4 is the most highly preferred drug carrier. The Fc domain of human origin is advantageous over that of non-human origin because the latter may act as an antigen in the body, inducing the production of antibodies thereto.

The present invention features the linkage of a protein drug to a dimeric protein via a non-peptidyl polymer.

In the present invention, the non-peptidyl polymer means a biocompatible polymer composed of two or more repeating units which are linked to each other via a covalent bond other than a peptide bond.

Conventional peptidyl linkers used in the fusion proteins prepared through in-frame fusion suffer from the disadvantage of being easily cleaved in vivo by proteinases to fail to guarantee the serum half life of the active drug as long as expected when the carrier remains intact. In contrast, the polymer of the present invention is resistant to enzymatic degradation, maintaining the serum half life of the drug as long as that guaranteed when the carrier remains intact. So long as it acts as mentioned above, that is, is resistant in vivo to proteinases, any polymer may be used in the present invention with no limitations imparted thereto. The non-peptidyl polymer useful in the present invention ranges in molecular weight from 1 to 100 kDa and preferably from 1 to 20 kDa. The non-peptidyl polymer of the present invention which is conjugated with an immunoglobulin Fc domain may be a polymer or a combination of different polymers.

Examples of the non-peptidyl polymer useful in the present invention include biodegradable polymers such as polyethylene glycol, polypropylene glycol, a copolymer of ethylene glycol and propylene glycol, polyoxyethylated polyol, polyvinyl alcohol, polysaccharide, dextran, polyvinyl ethyl ether, biodegradable polymers such as PLA (polylactic acid) and PLGA (polylactic-glycolic acid), lipopolymers, chitins, hyaluronic acid and combinations thereof, with a preference for polyethylene glycol. Also, their derivatives which are known in the art or which can be readily prepared using a typical technique fall within the scope of the present invention.

The non-peptidyl polymers used in the present invention have functional groups to which the immunoglobulin Fc domain and the protein drug can bind.

In contrast to the prior method for preparing protein complex using a non-peptidyl polymer having two functional ends (2-arm) (Korean Patent No. 10-0725315), the present invention employs a 3-armnon-peptidyl polymer. Different from the conventional non-peptidyl polymer which has one functional end and branches from a core molecule, the non-peptidyl polymer useful in the present invention has three functional ends in which two are responsible for the formation of covalent bonds with a dimeric protein while the other one is covalently linked to a physiologically active polypeptide.

In greater detail, because an immunoglobulin Fc is a homo-dimer with two N-termini in close vicinity to each other, respective links are formed between the two N-termini of the immunoglobulin Fc and the opposite termini of the non-peptidyl polymer. Thus, when the 2-arm non-peptidyl polymer first forms covalent bonds with the immunoglobulin Fc domain, there are no functional ends left that can be reacted with the physiologically active polypeptide, resulting in a significant decrease in production yield. Thus, the physiologically active polypeptide, prior to the 2-arm non-peptidyl polymer, is reacted with the immunoglobulin Fc domain. However, when the physiologically active polypeptide is reacted in advance, lots of undesirable impurities are produced, thus giving rise to the loss of the physiologically active polypeptide. In contrast, it is possible to react the 3-arm non-peptidyl polymer with immunoglobulin Fc domain before reaction with the physiologically active polypeptide because two of its three functional ends are responsible for two N-termini of the immunoglobulin Fc while the other functional end thereof can cover the physiologically active polypeptide. Hence, the protein complex can be produced in high yield. In practice, the production yield is found to increase two ~nine times more than when 2-arm non-peptidyl polymers are used.

The three terminal functional groups of the non-peptidyl polymer can bind to N-terminal, free lysine, histidine or cysteine residues of the immunoglobulin Fc domain and the physiologically active polypeptide.

Preferably, the three terminal functional groups of the non-peptidyl polymer are selected from among aldehyde groups, propionaldehyde groups, butyl aldehyde groups, maleimide groups and succinimide derivatives. Examples of the succinimide derivatives useful in the present invention include succinimidyl propionate, hydroxy succinimidyl, succinimidyl carboxymethyl and succinimidyl carbonate. Preferred are aldehyde groups. When present on the three termini of the non-peptidyl polymer, reactive aldehyde groups can minimize non-specific reactions and are effective in forming bonds with both the physiologically active polypeptide and the dimeric protein. Further, the final product formed by reductive alkylation with aldehyde is far more stable than is the product formed with amide bonds. Generally, aldehyde functional groups selectively react with amino ends at a low pH while forming a covalent bond with a lysine residue at high pH, e.g., pH 9.0. The three terminal functional groups of the non-peptidyl polymer may be the same or different from each other.

In accordance with the present invention, the conjugate of the dimeric protein with the non-peptidyl polymer is linked to a physiologically active polypeptide to form a protein complex.

Herein, the term "physiologically active polypeptide", "physiologically active protein", "active protein", "active polypeptide" or "protein drug" means a polypeptide, a peptide or a protein having some kind of antagonistic activity to a physiological event in vivo and these terms may be used interchangeably.

The physiologically active polypeptides applicable to the protein complex of the present invention may be exemplified by hormones, cytokines, interleukins, interleukin-binding proteins, enzymes, antibodies, growth factors, transcription factors, blood factors, vaccines, structural proteins, ligand proteins, receptors, cell surface antigens, receptor antagonists, and derivatives or analogs thereof.

Concrete examples of the physiologically active polypeptides useful in the present invention include human growth hormones, growth hormone releasing hormones, growth hormone releasing peptides, interferons and interferon receptors (e.g., interferon-α, -β and -γ, soluble type I interferon receptors), colony-stimulating factors, glucagon-like peptides (GLP-1, etc.), exendin-4 peptides, ANP (atrial natriuretic peptide), BNP (brain natriuretic peptide), CNP (c-type natriuretic peptide), DNP (dendroaspis natriuretic peptide), G protein-coupled receptors, interleukins (e.g., interleukin-1, -2, -3, -4, -5, -6, -7, -8, -9, -10, -11, -12, -13, -14, -15, -16, -17, -18, -19, -20, -21, -22, -23, -24, -25, -26, -27, -28, -29, -30) and interleukin receptors (e.g., IL-1 receptor, IL-4 receptor, etc.), enzymes (e.g., glucocerebrosidase, iduronate-2-sulfatase, α-galactosidase-A, α-L-iduronidase, butyrylcholinesterase, chitinase, glutamate decarboxylase, imiglucerase, lipase, uricase, platelet-activating factor acetylhydrolase, neutralendopeptidase, myeloperoxidase, etc.), interleukin- and cytokine-binding proteins (e.g., IL-18 bp, TNF-binding protein, etc.), macrophage activating factors, macrophage peptides, B-cell factors, T-cell factors, Protein A, allergy inhibitors, cell necrosis glycoproteins, immunotoxins, lymphotoxins, tumor necrosis factor, tumor suppressors, transforming growth factor, alpha-1 anti-trypsin, albumin, α-lactalbumin, apolipoprotein-E, erythropoietin, glycosylated erythropoietin, angiopoeitins, hemoglobin, thrombin, thrombin receptors activating peptides, thrombomodulin, blood factor VII, VIIa, VIII, IX and XIII, plasminogen activators, fibrin-binding peptides, urokinase, streptokinase, hirudin, Protein C, C-reactive protein, renin inhibitor, colagenase inhibitor, superoxide dismutase, leptin, platelet-derived growth factor, epithelial growth factor, epidermal growth factor, angiostatin, angiotensin, bone growth factor, bone stimulating protein, calcitonin, insulin, somatostatin, octreotide (somatostatin agonist), atriopeptin, cartilage inducing factor, elcatonin, connective tissue activating factor, tissue factor pathway inhibitor, follicle stimulating hormone, luteinizing hormone, luteinizing hormone releasing hormone, nerve growth factors (e.g., nerve growth factor, cilliary neurotrophic factor, axogenesis factor-1, glucagon-like-peptides (GLP-1), exendin-4 peptides, brain-natriuretic peptide, glial derived neurotrophic factor, netrin, neurophil inhibitor factor, neurturin, etc.), parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, myostatin, receptors (e.g., TNFR(P75), TNFR(P55), IL-1 receptor, VEGF receptor, B-cell activator receptor, etc.), receptor antagonists (e.g., IL1-Ra, etc.), cell surface antigens (e.g., CD 2, 3, 4, 5, 7, 11a, 11b, 18, 19, 20, 23, 25, 33, 38, 40, 45, 69, etc.), monoclonal antibodies, polyclonal antibodies, antibody fragments (e.g., scFv, Fab, Fab' F(ab')2 and Fd), and virus derived vaccine antigens. Preferably, the physiologically active polypeptide is selected from among human growth hormones, interferon-alpha, interferon-beta, granulocyte colony stimulating factor, erythropoietin, exendin-4, imidazole acetyl exendin-4 peptide (exendin-4 agonist), calcitonin, octreotide (somatostatin agonist), BNP and Fab'.

Disadvantageously, these protein drugs cannot maintain their biological activity in vivo over a long time because they are highly apt to denature or are readily degraded with proteinases. However, the complex of the present invention in which a dimeric protein and a polypeptide are conjugated via a non-peptidyl polymer increases both the structural stability and half clearance time of the drug. The reduction of the biological activity of the polypeptide because of conjugation with the dimeric protein is very insignificant, compared to that generated in conventional complexes. Therefore, the complex of the polypeptide and the immunoglobulin Fc domain in accordance with the present invention is characterized by having a significantly improved bioavailability, compared to that of conventional polypeptide drug agents.

In accordance with another aspect thereof, the present invention pertains to a method for preparing a protein complex in which a dimeric protein is conjugated with a physiologically active polypeptide via a 3-arm, non-peptidyl polymer, comprising: (1) covalently linking two arms of the 3-arm non-peptidyl polymer to opposite N-terminal amino groups of the dimeric protein to form a conjugate (2) isolating from the reaction mixture of step (1) the conjugate in which the dimeric protein is covalently linked at N-termini thereof with the non-peptidyl polymer and (3) covalently linking the physiologically active polypeptide to one free arm of the non-peptidyl polymer of the isolated conjugate.

In a preferred embodiment, the dimeric protein of step (1) is an immunoglobulin Fc domain. In another preferred embodiment, the three arms of the non-peptidyl polymer of step (1) have respective aldehyde functional groups at termini thereof. More preferably, the non-peptidyl polymer is linked to the N-terminal amino group of the physiologically active polypeptide at pH 6.0.

In step (1), the dimeric protein is reacted at a molar ratio of from 1:2 to 1:5 with the non-peptidyl polymer. In step (3), the molar ratio of the conjugate isolated by step (2): the physiologically active polypeptide preferably ranges from 1:0.5 to 1:0.05.

The reactions in steps (1) and (3) depend on the three terminal groups of the non-peptidyl polymer. If required, the reactions may be conducted in the presence of a reducing agent. Preferred examples of the reducing agent include sodium cyanoborohydride ($NaCNBH_3$), sodium borohydride, dimethylamine borate and pyridine borate.

The linkage between the immunoglobulin Fc domain and the physiologically active polypeptide is achieved not by fusion based on genetic recombination, but via a covalent bond.

In accordance with a further aspect thereof, the present invention pertains to a pharmaceutical composition comprising the protein complex of the present invention and a pharmaceutically acceptable vehicle, which shows an improvement in the in-vivo sustainability of a physiologically active polypeptide.

Via an appropriate route, the pharmaceutical composition of the present invention must be introduced into a tissue or organ of interest. So long as it is delivered to the targeted tissue, any route can be used for administration of the pharmaceutical composition of the present invention. For example, the administration may be carried out via intraperitoneal, intravenous, intramuscular, subcutaneous, intradermal, oral, local, intranasal, intrapulmonary, and intrarectal routes, but is not limited thereto. Preferably, the pharmaceutical composition of the present invention is administered in an injectable form. Also, the pharmaceutical composition may be administered with the aid of a device through which the active material is delivered to targeted cells.

The pharmaceutical composition based on the complex of the present invention may further comprise a pharmaceutically acceptable vehicle. For use as a pharmaceutically acceptable vehicle in oral dosage forms, a binder, a lubricant, a disintegrant, an excipient, a solubilizer, a dispersant, a stabilizer, a suspending agent, a colorant, and/or a fragment are selected. When the pharmaceutical composition of the present invention is formulated into injections, a buffer, a preservative, a pain relieving agent, a solubilizer, an isotonic, and a stabilizer may be used alone or in combination. For local application, a base, an excipient, a lubricant, and a preservative may be used. For practical use, the pharmaceutical composition of the present invention may be formulated in combination with the pharmaceutically acceptable vehicle into various dosage forms. For dosage forms, for example, it can be formulated into tablets, troches, capsules, elixir, suspensions, syrups, wafers, etc. As concerns injections, they may be in the form of single dose ampoules or multiple doses. Other available forms include solutions, suspensions, pills, powders, capsules, and sustained release agents. Examples of vehicles, excipients and diluents useful in the formulation include lactose, d-lactose, dextrose, sucrose, sorbitol, mannitol, xylitol, erythritol, maltitol, starch, acacia gum, alginate, gelatin, calcium phosphate, calcium silicate, cellulose, methyl cellulose, amorphous cellulose, polyvinyl pyrrolidone, water, methylhydroxybenzoate, propylhydroxybenzoate, talc, magnesium stearate and mineral oil. Also, a filler, an anti-agglomerating agent, a lubricant, a fragrant, an emulsifier, and a preservative are useful.

The pharmaceutically effective amount of the protein complex of the present invention varies depending on the kind of diseases to be treated, the route and frequency of administration, the age, gender and weight of the patient, and the severity of disease, as well as the kind of the physiologically active polypeptides. The superiority of the protein complex in in vivo persistency and titer makes it possible to reduce the administration dose and frequency of the pharmaceutical composition of the present invention.

As disclosed in Korean Patent Nos. 10-0725315 and 10-0775343, a protein complex is provided in which an immunoglobulin constant domain and a physiologically active polypeptide are respectively linked to opposite termini of a non-peptidyl polymer. This protein complex is prepared by linking the non-peptidyl polymer with the physiologically active polypeptide to form a conjugate and then with the immunoglobulin Fc. The preparation process is disadvantageous in that the physiologically active polypeptide is lost in a large quantity during the preparation. In contrast, the use of a 3-arm non-peptidyl polymer in the preparation of a protein complex can exceptionally reduce the loss of the physiologically active polypeptide. Further, the protein complex can be isolated using a simple purification method.

A better understanding of the present invention may be obtained through the following examples which are set forth to illustrate, but are not to be construed as limiting the present invention.

MODE FOR INVENTION

Example 1: Preparation of Immunoglobulin Fc-3 Arm PEG-Octreotide(N) Complex

For pegylation of an immunoglobulin Fc at its N-terminus, 10 mg/ml of immunoglobulin Fc was reacted at a molar ratio of 1:2 with 5K PropionALD (3) PEG (PEG with three propionaldehyde groups, NOF, Japan) at 4° C. for 4.5 hrs. The reaction was conducted in 100 mM potassium phosphate buffer, pH 6.0, in the presence of 20 mM SCB (NaCNBH$_3$) as a reducing agent. Using SOURCE Q (XK 16 ml, GE Healthcare), mono-pegylated immunoglobulin Fc was purified from the reaction mixture. Then, octreotide was reacted at a molar ratio of 1:2 with the immunoglobulin Fc-5K PEG conjugate at 4° C. for 20 hrs, with total protein concentration set at 25 mg/ml. This coupling reaction was carried out in 100 mM Potassium phosphate, pH 6.0, in the presence of the reducing agent 20 mM SCB. The coupling reaction mixture was purified through an SP HP purification column. Using a 10 mM sodium phosphate buffer (pH 5.4) as a binding buffer, the immunoglobulin Fc-5K PEG conjugate which did not undergo the coupling reaction was not attached to an SP HP column (XK 16 ml, GE Healthcare), but was separated by loading through the column, while the immunoglobulin-PEG-Octreotide (HM11760B) was attached slightly to the column and then eluted with a salt gradient of 1M NaCl.

Column: SP HP (XK 16 ml, GE Healthcare)
Flow rate: 2.0 ml/min
Gradient: A 0→20% 60 min B (A: 10 mM Na—P pH5.4, B: A+1M NaCl)

Example 2: Preparation of Immunoglobulin Fc-3 Arm PEG-Calcitonin (N) Complex

Immunoglobulin-Fc was reacted at its N-termini with 5K PropionALD (3) PEG in the same manner as in Example 1, after which only the mono-pegylated immunoglobulin Fc was purified and coupled with calcitonin. In this regard, calcitonin was reacted at a molar ratio of 1:2 with the immunoglobulin Fc-5K PEG conjugate at 4° C. for 20 hrs, with total protein concentration set at 25 mg/ml. For use as a medium in this coupling reaction, 100 mM potassium phosphate buffer, pH 6.0, was supplemented with the reducing agent 20 mM SCB (NaCNBH$_3$). The coupling reaction mixture was purified through an SP HP purification column. First, an SP HP column (XK 16 ml, GE Healthcare) was used to remove the immunoglobulin Fc-5K PEG conjugate which remained uncoupled with calcitonin. Using a 10 mM sodium phosphate buffer (pH 5.4) as a binding buffer, the immunoglobulin Fc-5K PEG conjugate which did not undergo the coupling reaction was not attached to an SP HP column (XK 16 ml, GE Healthcare), but was separated by loading through the column, while the immunoglobulin-PEG-calcitonin was attached slightly to the column and then eluted with a salt gradient of 1M NaCl.

Column: SP HP (XK16 ml, GE Healthcare)
Flow rate: 2.0 ml/min
Gradient: A 0→20% 60 min B (A: 10 mM Na—P pH5.4, B: A+1M NaCl)

Example 3: Comparison of Production Yield and Purification Process Simplicity Between 3 Arm PEG Complex (EXAMPLE 1 and 2) and 2 Arm PEG Complex Production yield of 3 arm PEG complex and 2 arm PEG complex was compared using the immunoglobulin Fc-3 arm PEG-Octreotide(N) complex and the immunoglobulin Fc-3 arm PEG-Calcitonin (N) complex prepared by EXAMPLE 1 and 2, respectively (table 1).

2 arm PEG complex as a control group was prepared by linking Octreotide or Calcitonin as a physiologically active polypeptide to the immunoglobulin Fc region via 2 arm PEG (PEG with two propionaldehyde groups, IDB, South Korea) as a linker. Particularly, a 2-arm PEG was coupled with Octreotide or Calcitoninand then with an immunoglobulin Fc domain via a covalent bond (KR10-0725315).

TABLE 1

| Active Pharmaceutical Ingredient (API) | PEG form | Production Yield (API basis) |
|---|---|---|
| Octreotide | 2 arm | 9% |
| | 3 arm | 33% |
| Calcitonin | 2 arm | 18% |
| | 3 arm | 30% |

The processes for purifying the complex from the coupling reaction mixture were analyzed for simplicity and primary column size and the results are summarized in Table 2, below.

TABLE 2

| API | PEG form | Purification Process | Size of Primary Column |
|---|---|---|---|
| Octreotide | 2 arm | Source Q -> Source ISO | 5 |
| | 3 arm | SP HP | 1 |
| Calcitonin | 2 arm | Source Q -> Source ISO | 4 |
| | 3 arm | SP HP | 1 |

When using the 2 arm PEG complex, all the immunoglobulin Fc which remained uncoupled was attached to the column so as to separate itself from the immunoglobulin Fc-2 arm PEG-Octreotide or the immunoglobulin Fc-2 arm PEG-Calcitonin. In contrast, when using the 3 arm PEG complex, separation between the immunoglobulin Fc-5K PEG conjugate which remained uncoupled with the physiologically active polypeptide and the immunoglobulin Fc-3 arm PEG-Octreotide or the immunoglobulin Fc-3 arm PEG-Calcitonin was achieved in such a manner that the immunoglobulin Fc-5K PEG conjugate was removed by loading through the column while the immunoglobulin Fc-3 arm PEG-Octreotide or the immunoglobulinFc-3 arm PEG-Calcitonin was attached to the column. Thus, not only was the purification process reduced from two steps to one, but also the column was ⅕ reduced in size.

Example 4: Preparation of Immunoglobulin Fc-3 Arm PEG-FSH(N) Complex

Immunoglobulin-Fc was reacted at its N-termini with 5K PropionALD (3) PEG in the same manner as in Example 1, after which only the mono-pegylated immunoglobulin Fc was purified and coupled with FSH. In this regard, FSH was reacted at a molar ratio of 1:15 with the immunoglobulin Fc-5K PEG conjugate at 4° C. for 20 hrs, with total protein concentration set at 40 mg/ml. For use as a medium in this coupling reaction, 100 mM potassium phosphate buffer, pH 6.0, was supplemented with the reducing agent 20 mM SCB. The coupling reaction mixture was purified through two purification columns. First, a Blue HP column (Hitrap 5 ml, GE Healthcare) was used to remove the immunoglobulin Fc-5K PEG conjugate which remained uncoupled with FSH. Subsequently, multi-polymers in which two or more immunoglobulin Fc-5K PEG conjugate were coupled with FSH were removed through Resource Iso (1 ml, GE Healthcare) on the basis of hydrophobicity.

Column: Blue HP (Hitrap 5 ml, GE Healthcare)
Flow rate: 3.0 ml/min
Gradient: A 0→100% 20 min B
A: 50 mM Gly-NaOH+0.2M KCl B: 50 mM Gly-NaOH+2.5M KCl
Column: Resource ISO (1 ml, GE Healthcare)
A 0→100% 90 min B (A: 20 mM Tris pH 7.5, B: A+1.3M A.S)

Example 5: Preparation of Immunoglobulin Fc-3 Arm PEG-Insulin (N) Complex

For pegylation of an immunoglobulin Fc at its N-terminus, 10 mg/ml of immunoglobulin Fc was reacted at a molar ratio of 1:2 with 5K PEG PropionALD (3) PEG (PEG with three propionaldehyde groups, NOF, Japan) at 4° C. for 4.5 hrs. The reaction was conducted in a 100 mM potassium phosphate buffer, pH 6.0, in the presence of 20 mM SCB (NaCNBH$_3$) as a reducing agent. Using SOURCE Q (LRC25 85 ml, GE Healthcare), mono-pegylated immunoglobulin Fc was purified from the reaction mixture. Then, insulin was reacted at a molar ratio of 1:4 with the immunoglobulin Fc-5K PEG conjugate at 4° C. for 19.5 hrs. For use as a medium for this coupling reaction, 100 mM potassium phosphate buffer, pH 6.0, was supplemented with the reducing agent 20 mM SCB. The coupling reaction mixture was purified through two purification columns. First, a SOURCE Q column (LRC25 85 ml, GE Healthcare) was used to remove the immunoglobulin Fc-5K PEG conjugate which remained uncoupled with insulin. A salt gradient of 1 M NaCl in 20 mM Tris (pH7.5) allowed the immunoglobulin Fc-5K PEG conjugate to be eluted first due to relatively weak binding force, immediately followed by the elution of immunoglobulin Fc-PEG-Insulin. Through this primary purification, immunoglobulin Fc-5K PEG conjugate was removed, but multi-polymers of Fc-5K PEG and Insulin were not separated completely. Secondary purification was thus conducted on the basis of difference in molecular weight between the complex and the multi-polymer using Sephacryl S-300 (GE Healthcare) column. At the same time, the immunoglobulin Fc-PEG-Insulin complex was formulated. High-molecular weight multi-polymers of immunoglobulin Fc-5K PEG and insulin were first eluted, followed by the immunoglobulin Fc-PEG-Insulin complex.

Column: Source Q (LRC25 85 ml, GE Healthcare)
Flow rate: 8.0 ml/min
Gradient: A 0→25% 100 min B (A: 20 mM Tris pH7.5, B: A+1M NaCl)
Column: Sephacryl S-300 (HiPrep 120 ml, GE Healthcare)
Flow rate: 0.6 ml/min

Example 6: Comparison of Production Yield Between 3 Arm PEG Complex (Example 4 and 5) and 2 Arm PEG Complex Production yield of 3 arm PEG complex and 2 arm PEG complex was compared using the immunoglobulin Fc-3 arm PEG-FSH(N) complex and the immunoglobulin Fc-3 arm PEG-Insulin (N) complex prepared by EXAMPLE 4 and 5, respectively (table 3).

When using the conventional preparation process using 2 arm PEG, dimeric physiologically active polypeptides, such as FSH (Mw. Ca. 40,000 Da) and insulin (Mw. 5,807), occupied both the termini of the non-peptidyl polymer so that the polymer could not form a covalent bond with the immunoglobulin Fc domain which provided persistence in vivo. This phenomenon was more conspicuous with a dimeric physiologically active polypeptide of small molecular weight, such as insulin.

Accordingly, persistent protein complexes with dimeric physiologically active polypeptides were preferably prepared using the 3 arm PEG.

Differences in the production yield of FSH and Insulin according to preparation process using 2 arm PEG and 3 arm PEG are summarized in Table 3, below.

TABLE 3

| Active Pharmaceutical Ingredient (API) | PEG form | Production Yield (API basis) |
|---|---|---|
| FSH | 2 arm PEG | 10% |
|  | 3 arm PEG | 32% |
| Insulin | 2 arm PEG | 3% |
|  | 3 arm PEG | 27% |

Example 7: Preparation of Immunoglobulin Fc-PEG-FacVIIa (N) Complex

For pegylation of an immunoglobulin Fc at its N-terminus, 6 mg/ml of immunoglobulin Fc was reacted at a molar ratio of 1:2 with 5K PropionALD (3) PEG (PEG with three propionaldehyde groups, NOF, Japan) at 4° C. for 4.5 hrs. The reaction was conducted in a 100 mM potassium phosphate buffer, pH 6.0, in the presence of 20 mM SCB (NaCNBH$_3$) as a reducing agent. Using SOURCE Q (LRC25 85 ml, GE Healthcare), mono-pegylated immunoglobulin Fc was purified from the reaction mixture. Then, FVIIa was reacted at a molar ratio of 1:9 with the immunoglobulin Fc-5K PEG conjugate at 4° C. for 18 hrs, with the total protein concentration set at 20 mg/ml. For use as a medium for this coupling reaction, a 100 mM potassium phosphate buffer, pH 6.0, was supplemented with the reducing agent 20 mM SCB. The coupling reaction mixture was purified through two purification columns. First, a SOURCE Q column (LRC25 85 ml, GE Healthcare) was used to remove the immunoglobulin Fc-5K PEG conjugate which remained uncoupled with FVIIa. A salt gradient of 1 M NaCl in 20 mM Tris (pH7.5) allowed the immunoglobulin Fc-5K PEG conjugate to be eluted first due to relatively weak binding force, immediately followed by the elution of immunoglobulin Fc-3 arm PEG-FVIIa. Thereafter, secondary purification was conducted to separate immunoglobulin Fc-3 arm PEG-FVIIa from FVIIa multimer impurities using a RESOURCE ISO (GE Healthcare) column. The immunoglobulin Fc-3 arm PEG-FVIIa was first eluted, followed by the FVIIa multimer impurities.

Column: Source Q (LRC25 85 ml, GE Healthcare)
Flow rate: 4 ml/min
Gradient: A 0→7% 1 min B, 7% 37% 80 min B (A: 20 mM Tris pH7.5, B: A+1M NaCl)
Column: RESOURCE ISO (Pre-packed 1 ml, GE Healthcare)
Flow rate: 2 ml/min
Gradient: B 100→0% 60 min A (A: 20 mM Tris pH7.5, B: A+1.6M (NH$_4$)$_2$SO$_4$)

TABLE 4

| Active Pharmaceutical Ingredient (API) | PEG form | Production Yield (API basis) |
|---|---|---|
| Fac VIIa | 2 arm PEG | Not prepared |
|  | 3 arm PEG | About above 3% |

Example 8: In-Vivo Assay of Immunoglobulin Fc-3 Arm PEG-Octreotide(N) Complex

The immunoglobulinFc-3 arm PEG-Octreotide(N) was assayed for ascertaining the effects on body weight and IGF-1 level in SD rats subcutaneously administered therewith. Octreotide is a potent inhibitor of growth hormone, and is mainly applied to the treatment of acromegaly. It is commercially available from Novartis in two forms: SANDOSTATIN™, a short acting version; and SANDOSTATIN-LAR™, a long acting version. Now, acromegaly is a syndrome that results upon the overproduction of human growth hormone (hGH). In in-vivo tests of octreotide, rats which are subcutaneously administered therewith are monitored for body weight and IGF-1 level to examine effects thereof on the inhibition of GH secretion. Likewise, the immunoglobulin Fc-3 arm PEG-Octreotide(N) was in vivo assayed for changes of body weight and IGF-1 level in rats. The immunoglobulin Fc-3 arm PEG-Octreotide(N) was administered in single doses of 0.5, 1.0, and 2.0 mg/kg while SANDOSTATIN-LAR™ as a control was administered in single doses of 1.0 and 2.0 mg/kg, after which the rats were monitored for body weight and IGF-1 level over two weeks. Both the two test materials were subcutaneously administered.

Compared to a vehicle-administered group, the SANDOSTATIN-LAR™ groups were observed to decrease in body weight by about 3.7% when administered with a dosage of 1.0 mg/kg and by about 8.9% when administered with a dosage of 2.0 mg/kg. On the other hand, the immunoglobulinFc-3 arm PEG-Octreotide(N) groups decreased in body weight by about 44.3% upon 0.5 mg/kg administration, by about 40.1% upon 1.0 mg/kg administration and by about 55.1% upon 2.0 mg/kg administration.

Quantitative analysis for IGF-1 changes in the rats used the rat IGF-1 ELISA kit. Compared to the vehicle, the blood IGF-1 level was observed to be decreased by about 15% with SANDOSTATIN 1.0 mg/kg and by about 11% with SANDOSTATIN 2.0 mg/kg on the basis of AUC of blood IGF-1 level. On the other hand, the immunoglobulin Fc-3 arm PEG-Octreotide(N) groups decreased in blood IGF-1 level by about 23% with a dosage of 0.5 mg/kg, by about 18% with a dosage of 1.0 mg/kg, and by about 25% with a dosage of 2.0 mg/kg [FIG. 2].

The in-vivo test data demonstrates that the immunoglobulin Fc-3 arm PEG-Octreotide(N) is more potent in activity than SANDOSTATIN-LAR™, a sustained formulation of octreotide.

Example 9: In-Vivo Assay of Immunoglobulin Fc-3 Arm PEG-FSH(N) Complex

In-vivo assay of the immunoglobulin Fc-3 arm PEG-FSH (N) was conducted according to the Steelman-Pohley method (Endocrinology 53, 504-616). Immature female SD rats (21 days old) were employed for in vivo assay of the immunoglobulinFc-3 arm PEG-FSH(N). The immunoglobulin Fc-3 arm PEG-FSH(N) was administered in single doses of 0.018, 0.075, and 0.3 μg/rat while Follitrope, a commercially available native form of FSH, was used as a control at dosages of 4, 2 and 1 IU/rat once per day for three days. A vehicle and the test materials were administered in combination with hCG (human chorionic gonadotropin) at 13.3 U/rat. Each test material was subcutaneously administered in an amount of 0.25 mL/kg. 72 hours after the first administration of the test materials, the animals were subjected to euthanasia and had an ovariotomy. The ovaries thus excised were weighed.

As depicted in FIG. 3, the immunoglobulin Fc-3 arm PEG-FSH(N) showed in vivo activity in a dose-dependent manner, with equality to the immunoglobulin Fc-2 arm PEG-FSH(N).

What is claimed is:

1. A protein complex, comprising
a physiologically active polypeptide,
a dimeric protein, and
a non-peptidyl polymer having three functional ends,
wherein both the physiologically active polypeptide and the dimeric protein are linked to the respective functional end of the non-peptidyl polymer via respective covalent bond,
wherein the dimeric protein is an immunoglobulin Fc domain, and
wherein the physiologically active polypeptide is selected from the group consisting of human growth hormone, growth hormone releasing hormone, growth hormone releasing peptide, interferon, interferon receptor, colony-stimulating factor, glucagon-like peptide, exendin-4 peptide, ANP (atrial natriuretic peptide), BNP (brain natriuretic peptide), CNP (c-type natriuretic peptide), DNP (dendroaspis natriuretic peptide), G protein-coupled receptor, interleukin, interleukin receptor, enzyme, interleukin-binding protein, cytokine-binding protein, macrophage activating factor, macrophage peptide, B-cell factor, T-cell factor, Protein A, cell necrosis glycoprotein, immunotoxin, lymphotoxin, tumor necrosis factor, tumor suppressor, transforming growth factor, alpha-1 anti-trypsin, albumin, a-lactalbumin, apolipoprotein-E, erythropoietin, highly glycosylated erythropoietin, angiopoietin, hemoglobin, thrombin, thrombin receptor activating peptide, thrombomodulin, blood factor VII, VIIa, VIII, IX or XIII, plasminogen activator, fibrin-binding peptide, urokinase, streptokinase, hirudin, Protein C, C-reactive protein, renin inhibitor, superoxide dismutase, leptin, platelet-derived growth factor, epithelial growth factor, epidermal growth factor, angiostatin, angiotensin, bone growth factor, bone stimulating protein, calcitonin, insulin, somatostatin, octreotide (somatostatin agonist), atriopeptin, cartilage inducing factor, elcatonin, connective tissue activating factor, follicle stimulating hormone, luteinizing hormone, luteinizing hormone releasing hormone, nerve growth factors, parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, myostatin, monoclonal antibody, polyclonal antibody, and Fab' fragment.

2. The protein complex as defined in claim 1, wherein the immunoglobulin Fc domain is aglycosylated.

3. The protein complex as defined in claim 1, wherein the immunoglobulin Fc domain is composed of one to four different domains selected from the group consisting of $C_H1$, $C_H2$, $C_H3$ and $C_H4$.

4. The protein complex as defined in claim 3, wherein the immunoglobulin Fc domain further comprises a hinge region.

5. The protein complex as defined in claim 1, wherein the immunoglobulin Fc domain is selected from the group consisting of Fc domains of IgG, IgA, IgD, IgE, IgM, and a combination thereof.

6. The protein complex as defined in claim 5, wherein the immunoglobulin Fc domain is selected from the group consisting of Fc domains of IgG1, IgG2, IgG3, IgG4, and a combination thereof.

7. The protein complex as defined in claim 5, wherein the immunoglobulin Fc domain is in a dimer or a multimer (combinations of immunoglobulin Fc), each comprising glycosylated immunoglobulin domains from the same origin.

8. The protein complex as defined in claim 6, wherein the immunoglobulin Fc domain is an IgG4 Fc domain.

9. The protein complex as defined in claim 8, wherein the immunoglobulin Fc domain is a human aglycosylated IgG4 Fc domain.

10. The protein complex as defined in claim 1, wherein the non-peptidyl polymer is selected from the group consisting of polyethylene glycol, polypropylene glycol, a copolymer of ethylene glycol and propylene glycol, polyoxyethylated polyol, polyvinyl alcohol, polysaccharide, dextran, polyvinyl ethyl ether, PLA (polylactic acid) and PLGA (polylactic-glycolic acid), lipopolymer, chitin, hyaluronic acid, and a combination thereof.

11. The protein complex as defined in claim 10, wherein the non-peptidyl polymer is a polyethylene glycol.

12. The protein complex as defined in claim 1, wherein each of the three functional ends of the non-peptidyl polymer has a functional group selected from the group consisting of an aldehyde group, a propionaldehyde group, a butyl aldehyde group, a maleimide group, and a succinimide derivative.

13. The protein complex as defined in claim 12, wherein the non-peptidyl polymer has three functional aldehyde groups at the three functional ends.

14. The protein complex as defined in claim 1, wherein the three functional ends of the non-peptidyl polymer bind to N-terminal, functional groups of the immunoglobulin Fc domain and the physiologically active polypeptide, said N-terminal, functional groups being selected from a group consisting of lysine, histidine, cysteine, and a combination thereof.

15. The protein complex as defined in claim 1, wherein the physiologically active polypeptide is selected from the group consisting of hormone, cytokine, interleukin, interleukin-binding protein, enzyme, antibody, growth factor, transcription factor, and blood factor.

16. The protein complex as defined in claim 1, wherein the physiologically active polypeptide is selected from the group consisting of human growth hormone, growth hormone releasing hormone, growth hormone releasing peptide, interferon and interferon receptor, colony-stimulating factor, glucagon-like peptide, exendin-4 peptide, ANP (atrial natriuretic peptide), BNP (brain natriuretic peptide), CNP (c-type natriuretic peptide), DNP (dendroaspis natriuretic peptide), G protein-coupled receptor, interleukin and interleukin receptor, enzyme, interleukin-binding protein, cytokine-binding protein, macrophage activating factor, macrophage peptide, B-cell factor, T-cell factor, Protein A, cell necrosis glycoprotein, immunotoxin, lymphotoxin, tumor necrosis factor, tumor suppressor, transforming growth factor, alpha-1 anti-trypsin, albumin, a-lactalbumin, apolipoprotein-E, erythropoietin, highly glycosylated erythropoietin, angiopoeitins, hemoglobin, thrombin, thrombin receptor activating peptide, thrombomodulin, blood factor VII, VIIa, VIII, IX and XIII, plasminogen activator, fibrin-binding peptide, urokinase, streptokinase, hirudin, Protein C, C-reactive protein, renin inhibitor, superoxide dismutase, leptin, platelet-derived growth factor, epithelial growth factor, epidermal growth factor, angiostatin, angiotensin, bone growth factor, bone stimulating protein, calcitonin, insulin, somatostatin, octreotide (somatostatin agonist), atriopeptin, cartilage inducing factor, elcatonin, connective tissue activating factor, follicle stimulating hormone, luteinizing hormone, luteinizing hormone releasing hormone, nerve growth factors, parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, and myostatin.

17. The protein complex as defined in claim 16, wherein the physiologically active polypeptide is selected from the group consisting of human growth hormone, interferon-alpha, interferon-beta, granulocyte colony stimulating factor, erythropoietin, exendin-4, imidazole acetyl exendin-4 peptide (exendin-4 agonist), calcitonin, octreotide (somatostatin agonist), and BNP.

18. A method for preparing a protein complex of claim 1 composed of a physiologically active polypeptide, a dimeric protein and a non-peptidyl polymer having three functional ends, with the linkage of both the physiologically active polypeptide and the dimeric protein to the respective functional end of the non-peptidyl polymer via respective covalent bond, comprising:

(1) covalently linking two of the three functional ends of the non-peptidyl polymer to respective N-terminal amino groups of the dimeric protein to form a conjugate, (2) isolating from the reaction mixture of step (1) the conjugate in which the dimeric protein is covalently linked at N-termini thereof with the non-peptidyl polymer and (3) covalently linking the physiologically active polypeptide to one free functional end of the non-peptidyl polymer of the isolated conjugate to obtain the protein complex.

19. The method as defined in claim 18, wherein the dimeric protein is an immunoglobulin Fc domain.

20. The method as defined in claim 18, wherein the non-peptidyl polymer has three functional aldehyde groups at the functional ends.

21. The method as defined in claim 18, wherein the dimeric protein is reacted with the non-peptidyl polymer in step (1) at a molar ratio ranges from 1:2 to 1:5.

22. The method as defined in claim 18, wherein the conjugate is reacted with the physiologically active polypeptide in step (3) at a molar ratio ranges from 1:0.5 to 1:0.05.

23. The method as defined in claim 18, wherein the reactions in both steps (1) and (3) are conducted in the presence of a reducing agent.

24. The method as defined in claim 23, wherein the reducing agent is selected from a group consisting of sodium cyanoborohydride (NaCNBH3), sodium borohydride, dimethylamine borate and pyridine borate.

25. A composition, comprising the protein complex of claim 1 and optionally a pharmaceutically acceptable vehicle.

26. The protein complex as defined in claim 1, wherein the protein complex is prepared by the method comprising:
(1) covalently linking two of the three functional ends of the non-peptidyl polymer to respective N-terminal amino groups of the dimeric protein to form a conjugate,
(2) isolating from the reaction mixture of step (1) the conjugate in which the dimeric protein is covalently linked at N-termini thereof with the non-peptidyl polymer and
(3) covalently linking the physiologically active polypeptide to one free functional end of the non-peptidyl polymer of the isolated conjugate to obtain the protein complex.

* * * * *